United States Patent
Molina Trigueros (10) Patent No.: US 7,288,100 B2
(45) Date of Patent: Oct. 30, 2007

(54) GASTRIC CLAMP FOR PERFORMING VERTICAL BAND GASTROPLASTY AND A GASTRIC BYPASS WITH LESSER CURVATURE

(75) Inventor: Luis Miguel Molina Trigueros, Madrid (ES)

(73) Assignee: Surgical-IOC, Saint Etienne (FR)

( * ) Notice: Subject to any disclaimer, the term of this patent is extended or adjusted under 35 U.S.C. 154(b) by 520 days.

(21) Appl. No.: 10/470,874

(22) PCT Filed: Jan. 30, 2002

(86) PCT No.: PCT/ES02/00039

§ 371 (c)(1), (2), (4) Date: Jul. 31, 2003

(87) PCT Pub. No.: WO02/064041

PCT Pub. Date: Aug. 22, 2002

(65) Prior Publication Data
US 2004/0097989 A1 May 20, 2004

(30) Foreign Application Priority Data
Feb. 12, 2001 (ES) .................. 200100306

(51) Int. Cl.
*A61B 17/08* (2006.01)
(52) U.S. Cl. .............. 606/151; 606/157
(58) Field of Classification Search ............ 606/151, 606/152, 153, 154, 155, 156, 157, 158, 120
See application file for complete search history.

(56) References Cited

U.S. PATENT DOCUMENTS

| 4,328,805 A | 5/1982 | Akopov et al. |
|---|---|---|
| 4,458,681 A | 7/1984 | Hopkins |
| 4,558,699 A * | 12/1985 | Bashour .................. 606/157 |
| 4,803,985 A | 2/1989 | Hill |
| 5,100,418 A * | 3/1992 | Yoon et al. .............. 606/139 |
| 5,345,949 A * | 9/1994 | Shlain .................... 128/898 |
| 5,549,621 A | 8/1996 | Bessler et al. |
| 5,843,098 A * | 12/1998 | Allen et al. .............. 606/144 |
| 6,206,897 B1 * | 3/2001 | Jamiolkowski et al. ..... 606/157 |

FOREIGN PATENT DOCUMENTS

EP 0519704 A1 12/1992

* cited by examiner

*Primary Examiner*—(Jackie) Tan-Uyen Ho
*Assistant Examiner*—Melanie Tyson
(74) *Attorney, Agent, or Firm*—DLA Piper US LLP (57) ABSTRACT

The invention relates to the production of a vertical gastric reservoir for the surgical treatment of morbid obesity. The reservoir consists of a clamp having two plates articulated at the lower end thereof and an automatic closing system in the upper part thereof, reinforced with a sealing system. Both plates are provided with two extensions (one at each end of the instrument) on the right-hand edge thereof. Both extensions are provided with two openings that are used to fix the instrument to the stomach wall. Application of the instrument and the technical solution provided are as follows: the substitution of metal staples which are subsequently eliminated in between 15% and 20% of patients and which result in failure of the vertical band gastroplasty operation. The instrument could also be used for producing small gastric reservoirs used for gastric bypass with minor curvature instead of metal staples.

5 Claims, 8 Drawing Sheets

PRIOR ART

GASTRIC CLAMP FOR PERFORMING VERTICAL BAND GASTROPLASTY AND A GASTRIC BYPASS WITH LESSER CURVATURE

OBJECT OF THE INVENTION

This invention refers to an instrument that would permit the substitution of the stapling of the V.B.G. and, eventually, a gastric by-pass with a minor curvature (in patients operated on for Morbid Obesity by means of these procedures), by a clamp capable of efficiently compressing the front and rear gastric wall, in a manner parallel to the minor curvature, in this way preparing the small gastric reservoir.

BACKGROUND TO THE INVENTION

Morbid Obesity is a serious health problem that affects more than 4 million people in the U.S.A. In Spain, it is calculated that it affects 2% of the population and is progressively more frequent, just as it is world level. Morbid Obesity decreases the life expectance of the subjects that by merely suffer it "per se", but also as a predisposing factor of other pathologies, such as diabetes mellitus, arterial hypertension, myocardial ischemia, obstructive sleep apnoea syndrome (O.S.A.S., osteo-articular pathology . . . )

The only efficient treatment is Surgery, that is indicated when the Body Mass Index (B.M.I.) is greater than 40 (B.M.I.=Weight in Kg/Height in $m^2$) or when the B.M.I. is greater than 35, when the so-called co-morbidities exist (hypertension, diabetes, myocardial ischemia, O.S.A.S . . . ).

Among the most used surgical treatments, we highlight Vertical Band Gastroplasty (V.B.G.), which consists of producing a small gastric reservoir that causes the patient to experience "early satiation" in the ingestion of food, therefore restricting the capacity for gastric ingestion and storage, with which a very considerable loss of weight is achieved.

The V.B.G. is a simple and efficient technique in the decade of the eighteenths and supposed more than 80% of the baryatric surgery interventions in the U.S.A., but presented a serious problem that has still not been satisfactorily resolved: the elimination of the staples, that condition the production of reservoir-gastric fistulas and which, in the final term, lead the patient regaining weight. This has had an influence on the resurgence or search of other more complex alternative surgeries (Gastric by-pass, sphincter of Oddi derivation, . . . ) with greater surgical risk.

Figure 1:
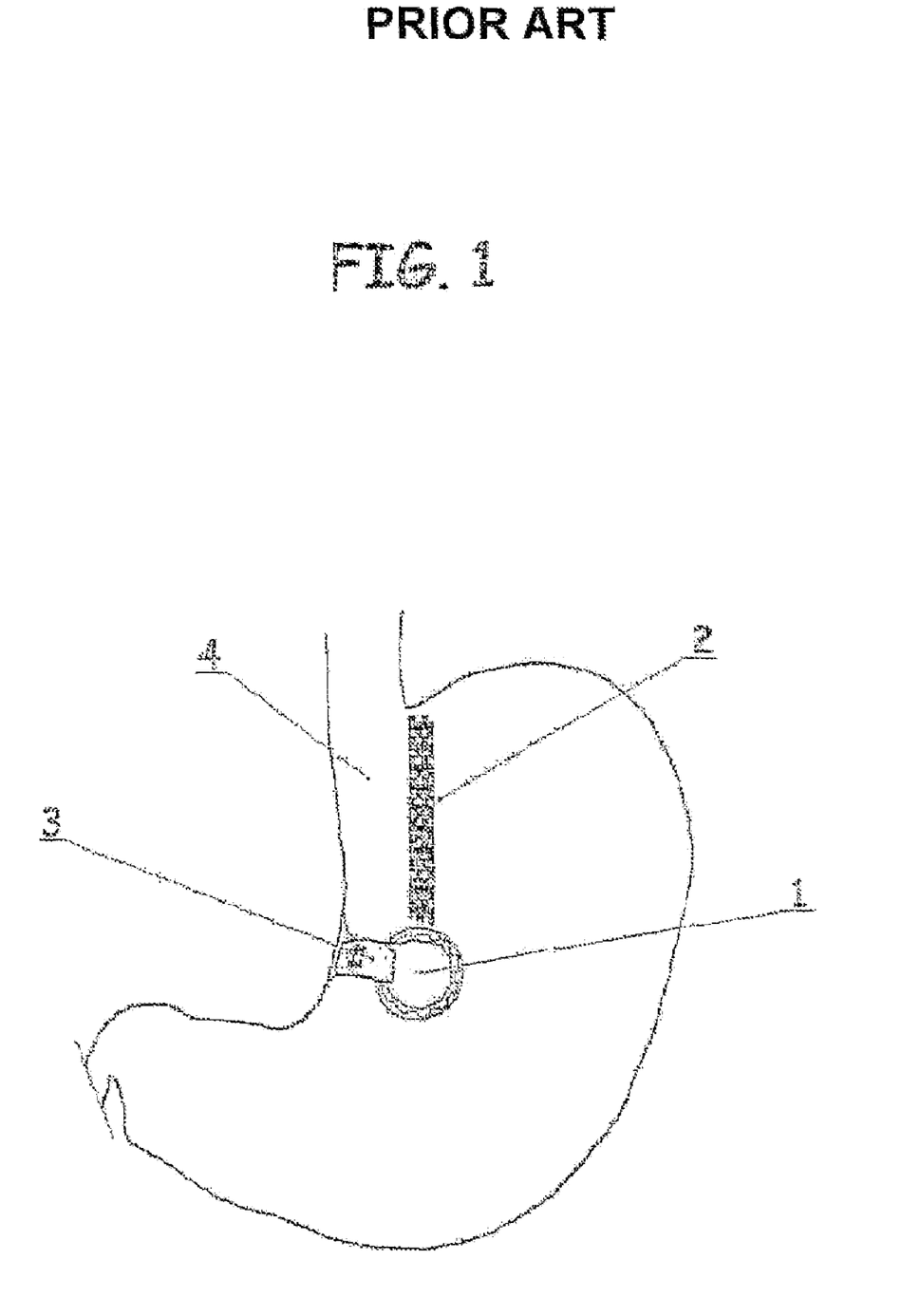
FIG. 1 represents a V.B.G just as it is carried out at present in bariatric surgery, in order to compare and understand the different characteristics originated in this invention.
Figure 2:
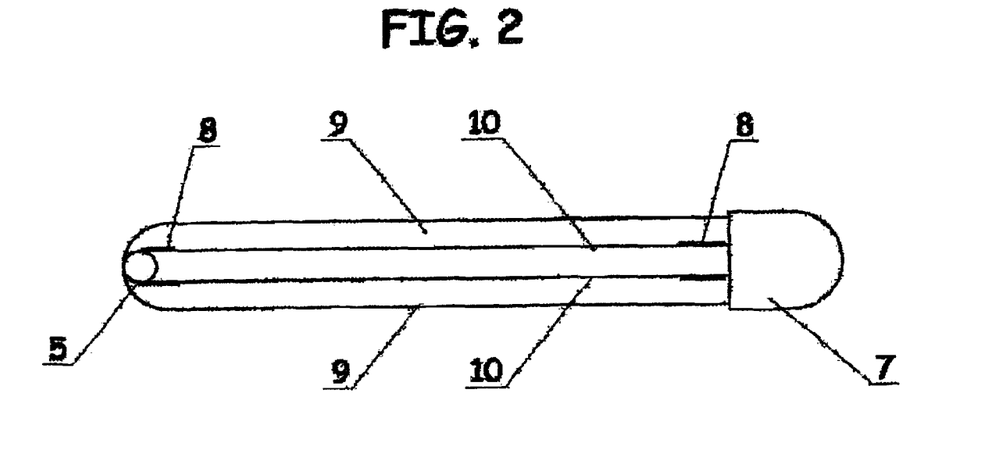
FIG. 2 shows a view of the right side elevation of the clamp in a closed position. Note: The left side elevation is similar to that of FIG. 2, except that it does not have any wider parts for fixing the clamp.
Figure 3:
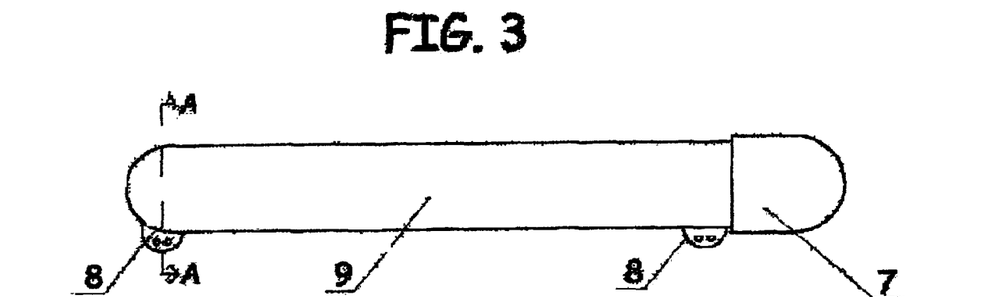
FIG. 3 shows the main level of the clamp.
Figure 4:
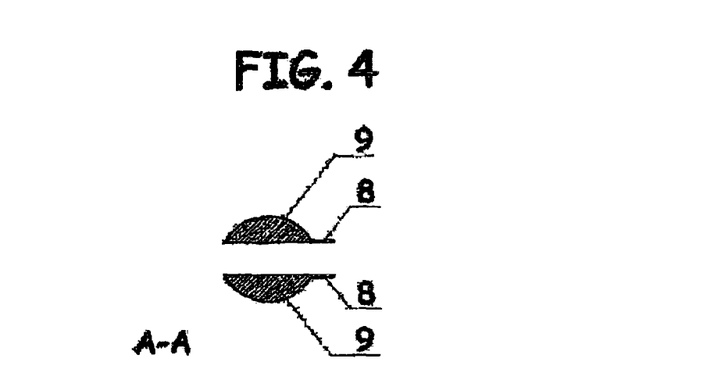
FIG. 4 shows a section of the clamp at the A-A' level.
Figure 5:
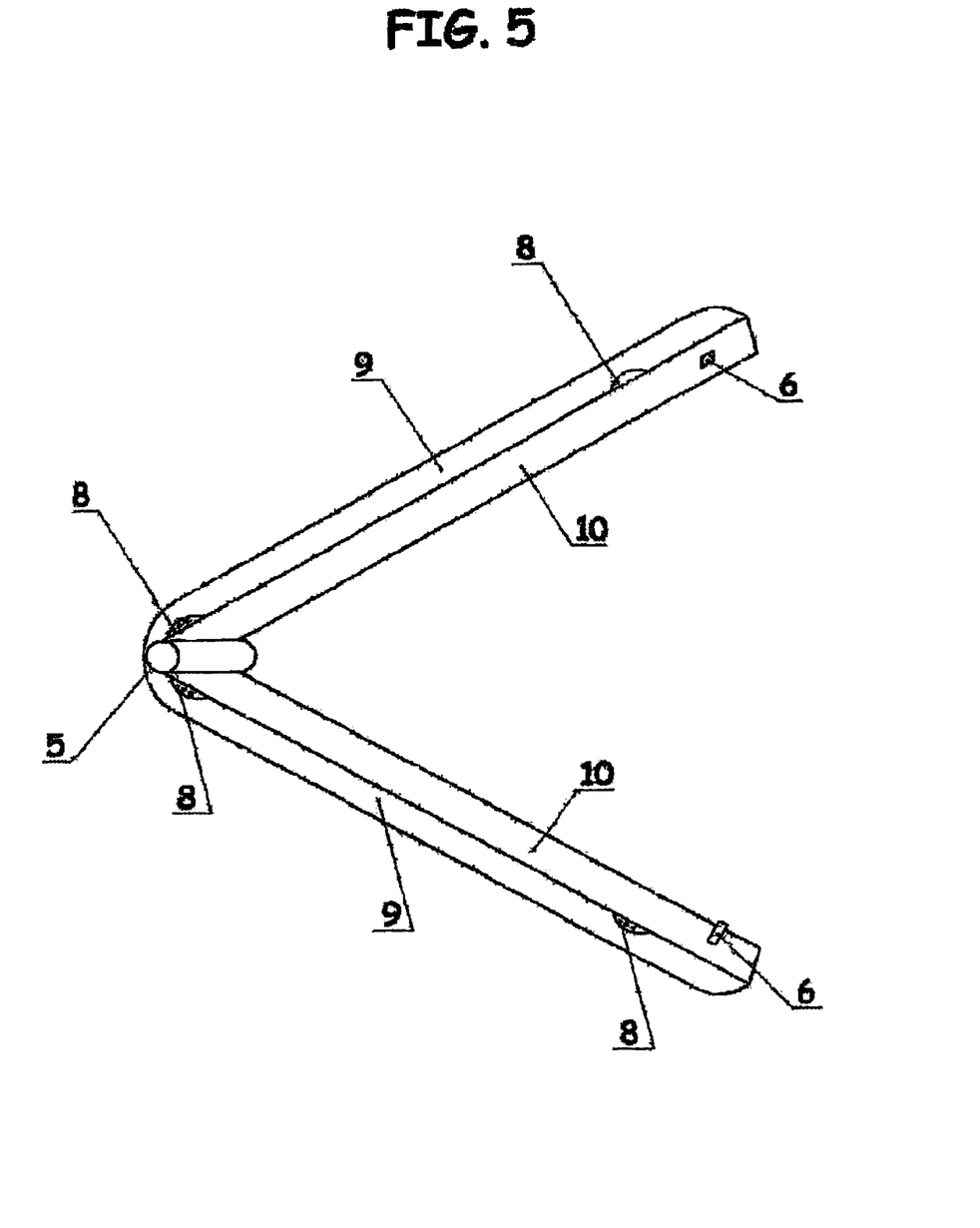
FIG. 5 shows a view of the right side elevation of the clamp, in the open position at an angle of 45°, although the rotation on the axle must reach 180°, as described in its moment.

The V.B.G. (FIG. 1) consists of vertical gastric stapling (2) (performed by means of the baryatric stapler) parallel to the minor curvature, with a previous preparation of a "gastric window" (1) in 6-7 cm of oesophageal-gastric union which, as well as permitting the later stapling of the viscera, permits the location of a band (3) (Marlex, P.T.F.E. . .) that notably decreases the capacity of gastric filling, limiting it to the small gastric reservoir (4) and, in the final term, making it difficult for food to pass to the rest of the viscera.

The gastric stapling is performed with the baryatric A.T. that establishes 4 rows of metal staples and some authors have employed double staples (8 rows of staples, partially over-imposed), to avoid the after reservoir-gastric fistulas previously mentioned where possible. This approach decreased the incidence by 15%-20% to 5%-10%, but did not eliminate it completely.

Some American patents have designed instruments for executing gastroplasties:

Hopkins in 1982 (U.S. Pat. No. 4,458,681) designed a clamp for performing a horizontal Gastroplasty, with a separation of the two plates in the central area, to permit food to pass to the distal gastric area. To my knowledge, this has not been used in a clinic. In any case, horizontal gastroplasties in general have not demonstrated any efficiency in the treatment for Morbid Obesity.

More recently, Bessler in 1995 (U.S. Pat. No. 5,549,621) designed a sophisticated instrument to perform a V.B.G. that includes two metal bars that have penetrating points that protrude from the first clamp, to join the "receiver" clamp, totally crossing the gastric wall. This instrument includes the V.B.G. exit band. To my knowledge, it has not been used in a clinic. In neither of the descriptions did the instrument have an external curvilinear configuration, with blunt edges nor is it covered with a material that cushions the pressure of the plates or bars. In neither of the descriptions did the instrument have an external curvilinear configuration, with blunt edges nor is it covered with a material that cushions the pressure of the plates or bars.

Thus, the present alternative in Surgery to the instrument that is the object of the invention is the baryatric Stapler, that locates the metal staplers and the plates with points that completely cross the gastric wall (with respect to the last instrument, no clinical experience exists).

EXPLANATION OF THE INVENTION

The object of the gastric clamp for performing a vertical band gastroplasty has the objective of resolving the problem produced by the elimination of staples, that is, reservoir-gastric fistulas, in patients who have been operated on using this surgical procedure. The gastric "window" and the band at the far end of the gastric reservoir has a significance and preparation identical to that of the conventional V.B.G. technique.

This clamp, the object of the invention, is formed of:
   2 articulated plates 8.5 cm in length and 10 mm wide, articulated at their lower end, by means of a hinge with a stop, that permits a rotation of 180° and with an automatic closing system at the upper end, that permits the clamp to be closed completely, all the instrument compressing the front and rear walls of the stomach, with a uniform pressure between the two plates.
   A "sealing" system that reinforces the automatic closing system of the instrument and, in the case of a sudden increase of pressure in the interior of the gastric reservoir (produced by vomiting, which is not at all infrequent in these patients who have been operated on for a V.B.G.) preventing the automatic closing system from opening. This sealing system is formed of a "female" part that covers the upper end of the clamp in the "closed" position.
   The two plates have two wider parts (one on each end of the instrument) on the right edge. The two wider parts have two holes to make it possible to fix the instrument to the gastric wall, by means of suture points, in order to avoid later movement of the clamp.
   As the clamp has to remain in the patient's body after surgery, a weight of small weight is preferred for its design, of light alloy and highly resistant, that is easily tolerated by the organism and titanium complies with all these conditions although an inert plastic material can also be used, as the frame or body of the instrument.
   As the stomach is a soft viscera that does not have any consistency and is even less similar to bone tissue, the entire clamp: 1) has blunt or curved edges throughout its external configuration, except in the area of contact with the stomach (internal surface), which is flat. This design will avoid the production of decubitus in the gastric viscera or adjacent structures. 2) is totally lined with material well tolerated by the organism and which, at the same time, conveniently cushions the pressure exercised by the plates of the clamp, on the front and rear gastric wails. The surface materials proposed are TEFLON.

Eventually, this clamp will also be able to be used in the gastric By-pass with a minor curve, as can be appreciated in the corresponding drawing and its width of 10 mm will permit an instrument to pass via a puncture needle of 12 mm, to position it by means of Laparoscopic Surgery.

The advantages of the object that is the object of the invention are:

Simple technique and easy preparation of the gastric reservoir, both in the V.B.G. and in the gastric By-pass with a minor curve.

Substitution of the staples in the baryatric stapler, by the gastric clamp described, which eliminates the possibility of staples escaping and gastric reservoir fistulae and, therefore, failure of the surgical treatment.

EXPLANATIONS OF THE DRAWINGS

For better understanding of that described in this report, technical drawings of the instrument and their location in the stomach are included.

DETAILED DESCRIPTION OF THE INVENTION

The gastric clamp described for the creation of a V.B.G. substitutes the gastric stapling made with the baryatric TA -2- With regard to the gastric "window" -1- and the PTFE band -3- in the lower end of the reservoir -4-, they have a special significance and identical preparation to that for the conventional technique employed at present in surgery for morbid obesity.

The gastric clamp that is the object of this invention is formed of two plates of 8.5 cm long and 10 mm wide. Of these dimensions, the first has a relation with the length of the gastric reservoir and the second, bringing a surface of pressure sufficient for guaranteeing the watertight integrity of the gastric reservoir with respect to the rest of the viscera, at the time that the area of the gastric fabric that compresses the viscera is not excessive extensive, in order to prevent an ischemia or vascularisation deficit of the stomach, that causes a necrosis of the gastric wall. Previous evidence confer an advantage in this sense to pressure with clamps or bars over stapling as the pressure exercised on the gastric wall in contact with the bar is distributed uniformly over the surface, where in the stapling, the action of the pressure is only exercised in areas in which the viscera is penetrated by staples.

Both plates are articulated in their lower end, by means of a hinge system -5- with a stop that permits a rotation of 180° over their axis (to achieve easy and convenient location, at the same time that their positioning is permitted by means of laparoscopic surgery via a 12 mm puncture needle).

At the upper end, the two plates have an automatic closing system (brace) -6- that permits the closing of the clamp to be completed, the entire instrument compressing the front and back walls of the stomach, with a uniform pressure between the two plates.

The automatic closing system is reinforced with a sealing system -7-, to prevent any sudden increase in intra-gastric pressure causing the opening of the clamp. This system of "sealing" consists of a female part that embraces the upper end of the clamp for a length of 1.25 cm, with the latter being in the closed position.

The two plates, at the tow ends, have two wider parts on the right edge (the one that is located in the gastric side opposite the small gastric reservoir). The two wider parts have two holes -8- that make it possible to fix the instrument to the gastric wall, by means of re-absorbable suture points, both on the upper edge and on the lower edge of the stomach adjacent to the reservoir (fundus of the stomach and the gastric "window" previously produced), in order to avoid later displacements of the clamp.

As stated, the material is of light alloy, of little weight, high resistance and bio-compatible (titanium or inert plastic material). Throughout the external configuration, the edges are blunt or curved -9-, except in the area of contact with the stomach (internal surface), where they are flat -10-. The entire instrument is covered in a material that suitably cushions the pressure exercised by the plates of the clamp, on the front and rear gastric walls and does not cause the organism to reject it. The materials proposed are P.T.F.E. or TEFLON.

Figure 6:
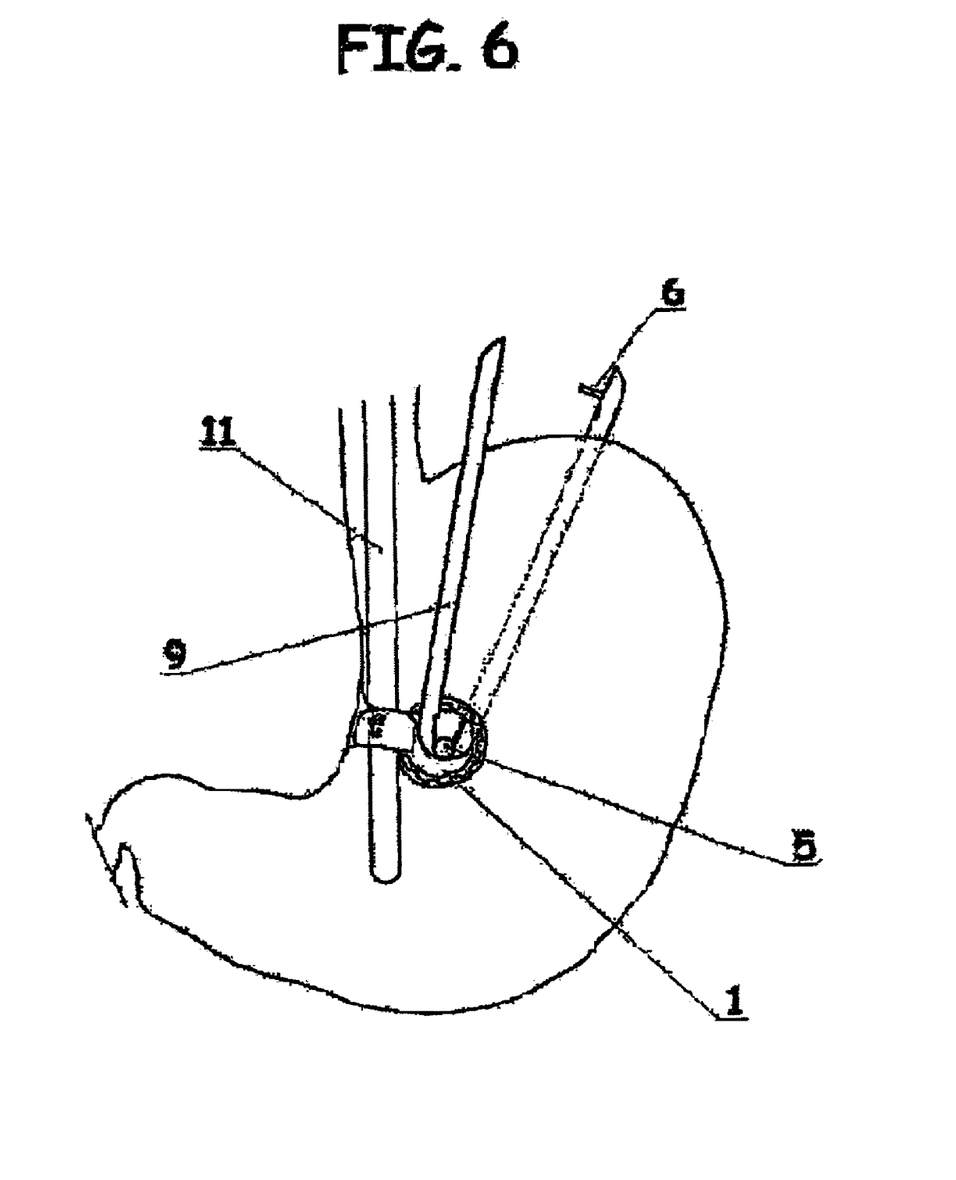
FIG. 6 shows a view of the clamp, in the open position, in the process of positioning on the stomach. The diameter of the gastric reservoir is adjusted by means of a Fouchet probe of No. 32, just as for conventional surgery.
Figure 7:
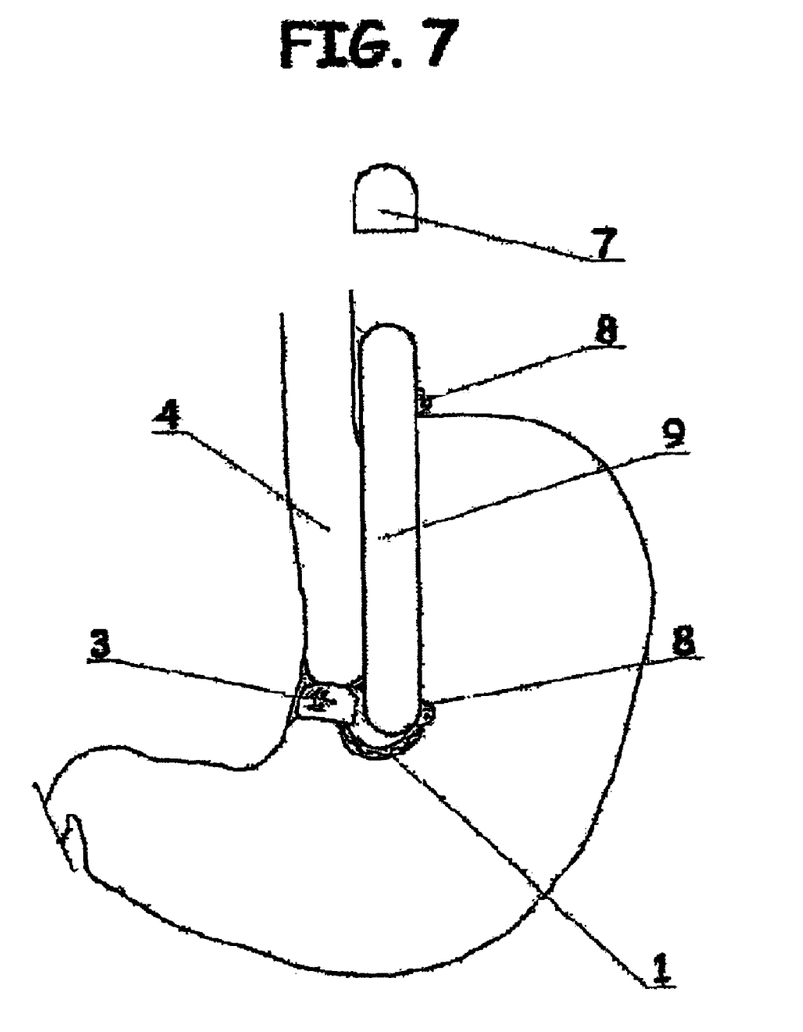
FIG. 7 shows a view of the clamp, once positioned and closed on the stomach and the female reinforcing part that is going to the introduced in the upper end of the clamp.
Figure 7A:
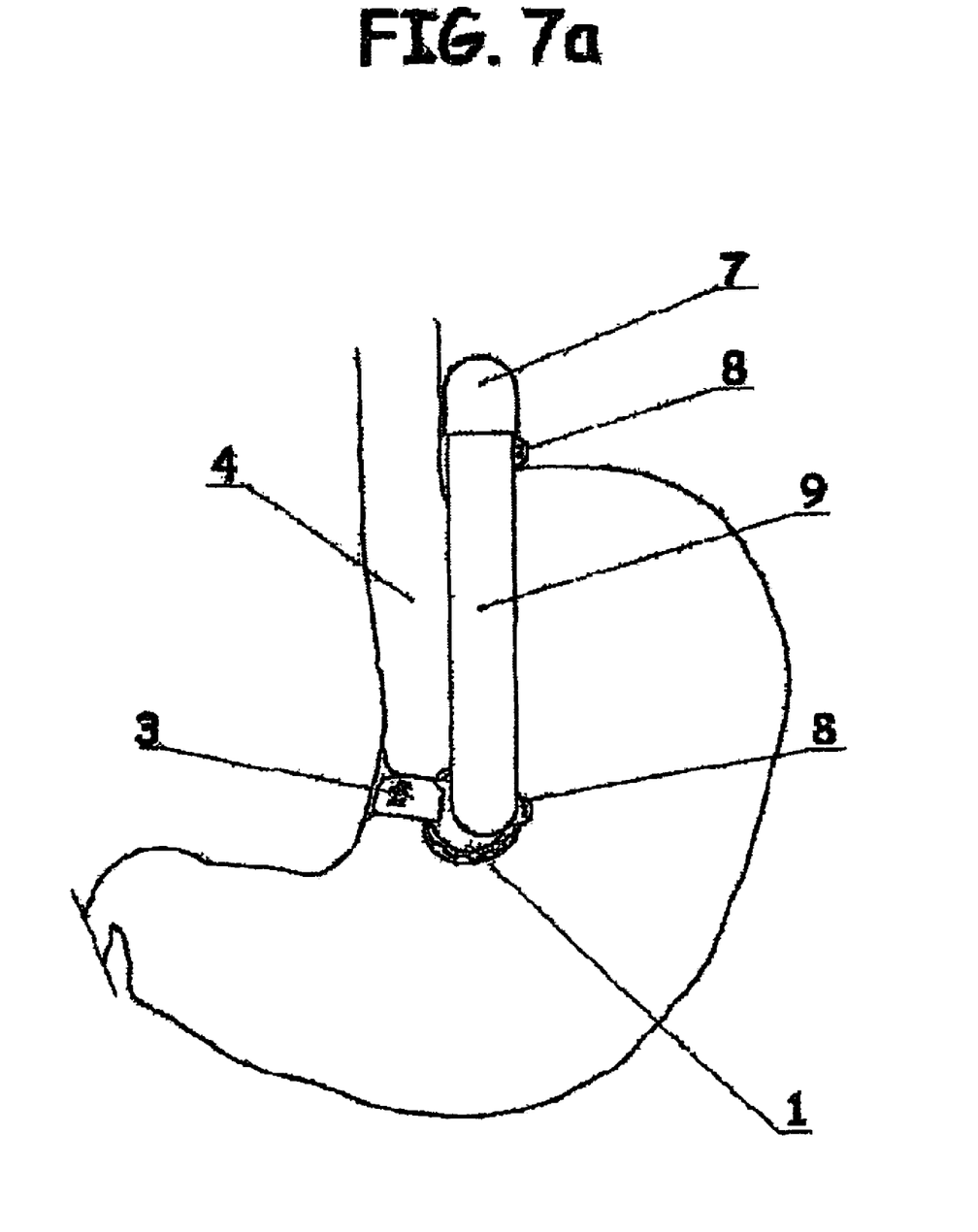
FIG. 7a shows the female sealing or reinforcing part, once positioned in the upper end of the clamp.

Its surgical positioning in the V.B.G. is carried out in the following manner—FIGS. 6, 7 and 7a-. Once the gastric "window" has been produced, by means of the CEEA circular auto-suture machine No. 28, the rear plate is introduced behind the stomach, until it assumes its upper end above the fundus of the stomach, then proceeding to the automatic closing of the instrument. Once this has been performed, the female part of the sealing system is included. The instrument continues a vertical direction towards the oesophagus and Hiss angle and the diameter of the gastric reservoir is adjusted by means of a Fouchet probe -11 - size No. 32, the same as for conventional surgery. Once the clamp has been positioned and closed over the stomach, this is fixed, passing some button sutures via the wide areas of the instrument -8-, over the fundus and the gastric wall, on the gastric side opposed to the reservoir. The Fouchet probe is removed and the P.T.F.E. band is located at the distal end of the reservoir, the same as standard surgery.

Figure 8:
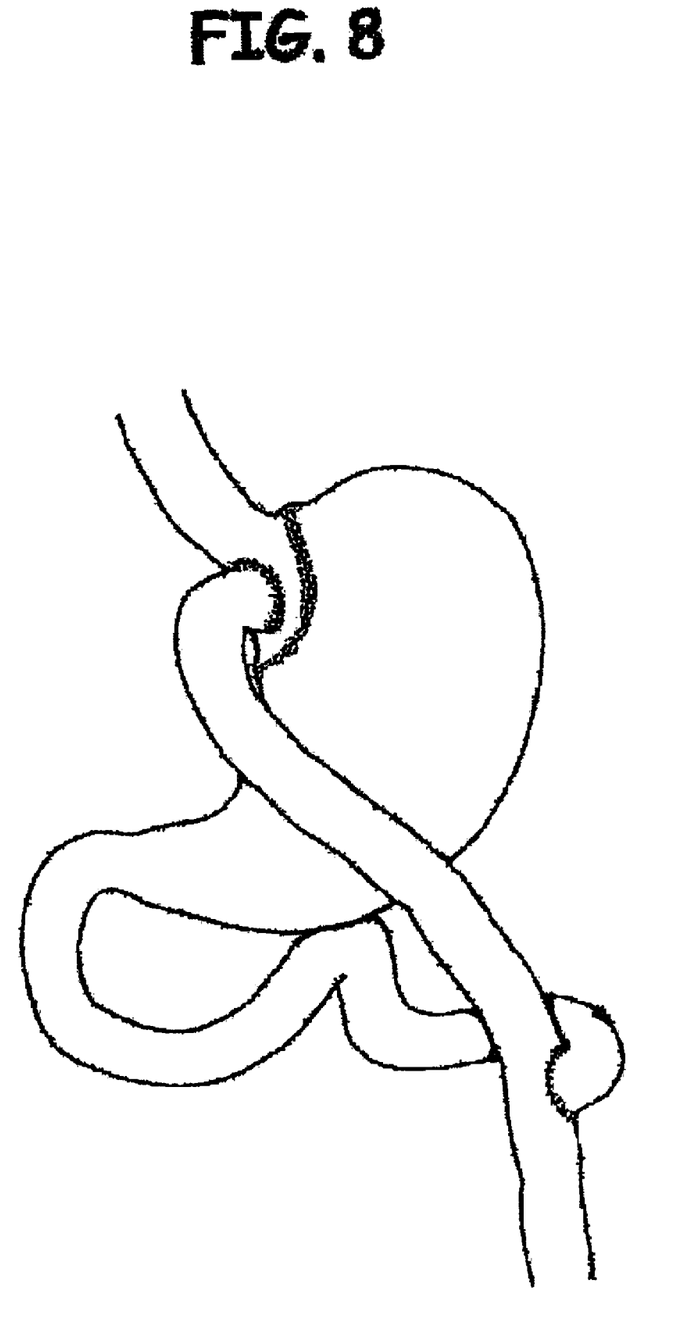
FIG. 8 shows a front view of a gastric by-pass with a minor curvature (Torres-Oca Technique), as carried out in bariatric surgery
Figure 9:
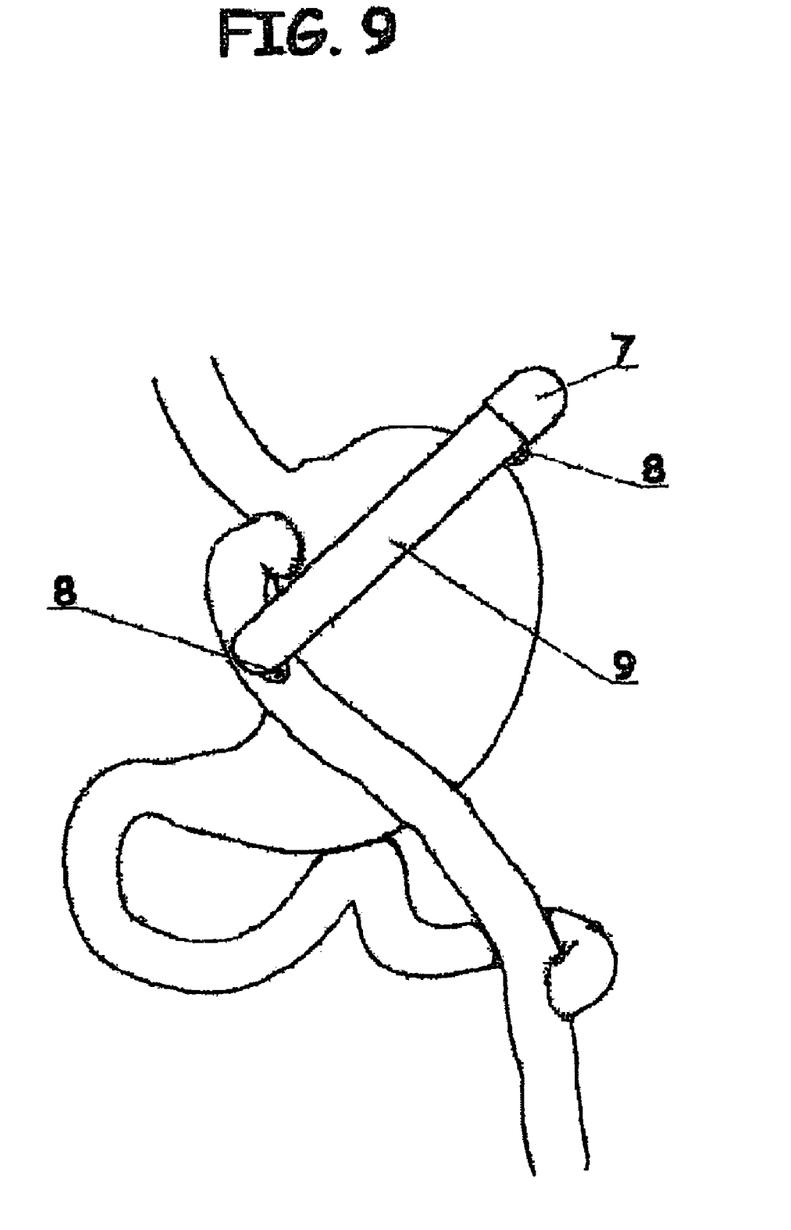
FIG. 9 shows a view of the optional application for the instrument described, embracing the front and rear walls of the stomach (in the most inclined position of the V.B.G.), in substitution for the gastric stapling.

Eventually, this clamp can also be used in the gastric By-pass with a minor curve (FIG. 8), as can be seen in FIG. 9 and its width of 10 mm would permit an instrument to pass via a 12 mm puncture needle, to position it by means of laparoscopic surgery.

The invention claimed is:

1. Gastric clamp for Vertical Band Gastroplasty (V.B.G.) and gastric By-pass with a minor curve and a cushioned surface comprising a frame in which two articulated plates, an automatic closing system at an end of both plates, a sealing or reinforcement system in the form of a female part that embraces an open end of the plates along a length of 1.25 cm once the plates are in the closed position, a curvilinear configuration of blunt edges with a flat internal surface, a system for fixing the plates to the stomach located on a right edge of each plate having a wide part located on an upper end of each plate and a wide part located on a lower end of each plate, each wide part having two holes that allow for the passage of button sutures, and an overall covering are included, whereby both plates are articulated at the lower end by means of a hinge system with a stop that permits rotation of 180 degrees over the axis.

2. Gastric clamp according to claim 1, wherein the entire clamp is manufactured in titanium or in an inert plastic material.

3. Gastric clamp according to claim 1, wherein the entire clamp is covered in P.T.F.E. or TEFLON.

4. Gastric clamp according to claim 2, wherein the plates are 8.5 cm in length and 10 mm wide.

5. Gastric clamp according to claim 3, wherein the plates are 8.5 cm in length and 10 mm wide.

* * * * *